(12) United States Patent
Larm et al.

(10) Patent No.: US 6,207,653 B1
(45) Date of Patent: Mar. 27, 2001

(54) USE OF HEPARIN OR HEPARAN SULPHATE IN COMBINATION WITH CHITOSAN FOR THE PREVENTION OR TREATMENT OF INFECTIONS CAUSED BY HERPES VIRUS

(75) Inventors: Olle Larm, Bromma; Marcus Back, Vällingby; Tomas Bergström, Sävedal, all of (SE)

(73) Assignee: Medicarb AB, Bromma (SE)

( * ) Notice: Subject to any disclaimer, the term of this patent is extended or adjusted under 35 U.S.C. 154(b) by 0 days.

(21) Appl. No.: 09/230,021
(22) PCT Filed: Aug. 1, 1997
(86) PCT No.: PCT/SE97/01320
 § 371 Date: Jan. 19, 1999
 § 102(e) Date: Jan. 19, 1999
(87) PCT Pub. No.: WO98/05341
 PCT Pub. Date: Feb. 12, 1998
(30) Foreign Application Priority Data Aug. 6, 1996 (SE) .................................................. 9602931

(51) Int. Cl.⁷ ........................ A01K 43/04; A61K 31/715
(52) U.S. Cl. .................. 514/55; 514/56; 514/57
(58) Field of Search ................................... 514/56, 55, 57

(56) References Cited

U.S. PATENT DOCUMENTS 4,465,666 * 8/1984 Lukas et al. ......................... 424/145

FOREIGN PATENT DOCUMENTS

| 0000133A1 | 1/1979 | (EP) | ............... | A61K/33/30 |
| 0240098A2 | 10/1987 | (EP) | ............... | A61K/31/70 |
| 0497341A2 | 8/1992 | (EP) | ............... | A61K/37/02 |

OTHER PUBLICATIONS

Takizawa et al 117 CA:178315, 1992.*
Baba et al 110CA:349, 1988.*

* cited by examiner

*Primary Examiner*—Russell Travers
(74) *Attorney, Agent, or Firm*—Burns, Doane, Swecker & Mathis LLP

(57) ABSTRACT

The use of heparin or heparan sulphate in combination with chitosan for the manufacture of a medicament for the prevention or treatment of infections caused by herpes virus in mammal including man; and a process for the treatment of infectious diseases caused by herpes viruses.

13 Claims, 1 Drawing Sheet

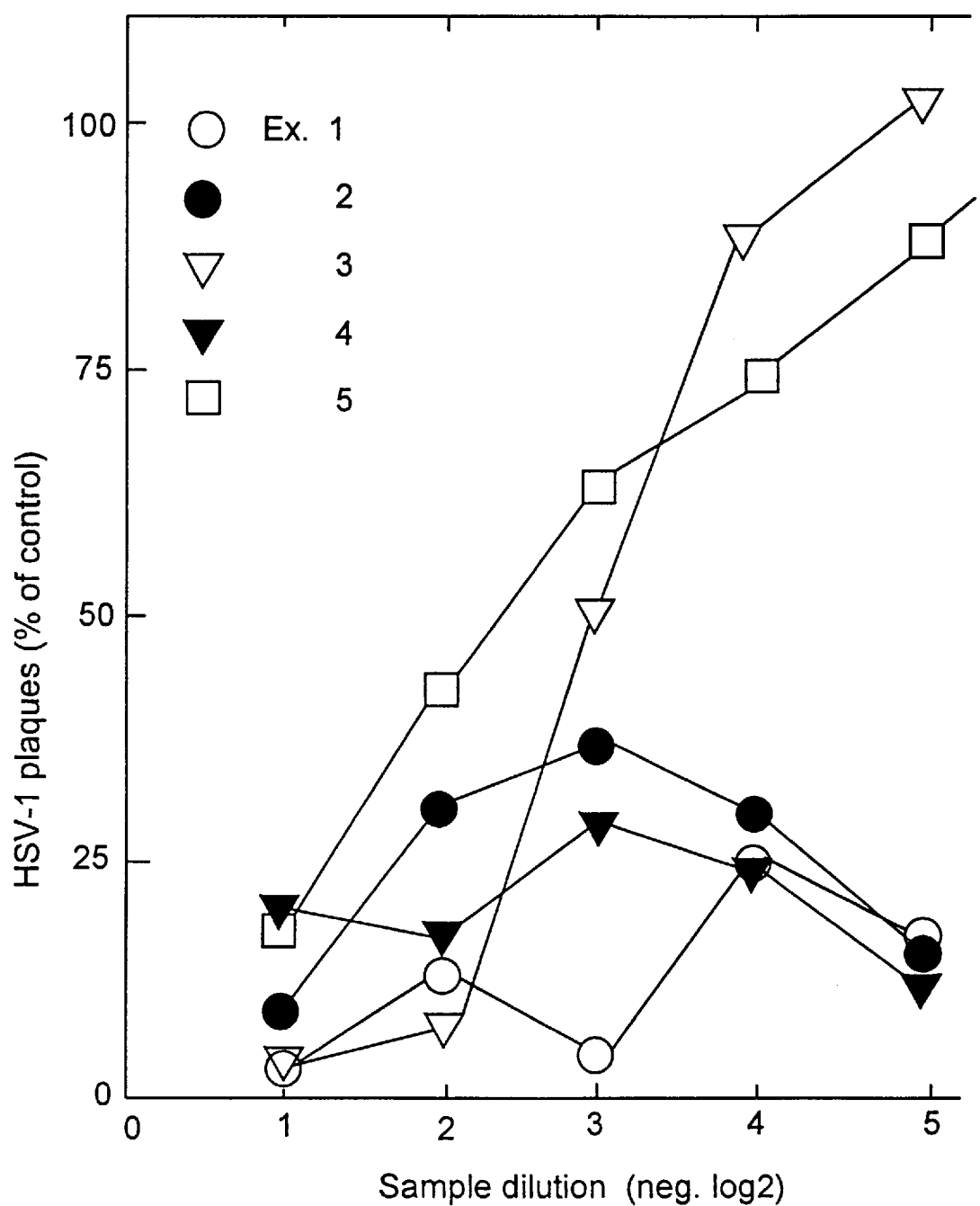

USE OF HEPARIN OR HEPARAN SULPHATE IN COMBINATION WITH CHITOSAN FOR THE PREVENTION OR TREATMENT OF INFECTIONS CAUSED BY HERPES VIRUS

This application is a 371 of PCT/SE97/01320 filed Aug. 1, 1997 which claims priority from Swedes Application No. 9602931-9 filed Aug. 6, 1996.

TECHNICAL AREA

The present invention refers to the use of certain sulphated polyanionic glucoseaminoglycans for the manufacture of medicaments that can be used for preventing or treating infections caused by herpes virus.

BACKGROUND OF THE INVENTION

Herpes is the common name for a family of viruses which generate infectious disease in mammals including man. Contrary to the majority of infections herpes viruses usually generate what is called latent infections, thus residing dormant in nerve roots of the central nervous system and subsequently causing active disease when activated by some unknown factor. There is today no method available for the treatment of such infections. Factors activating the disease are mostly unknown but it is believed that stress, fever, menstruation, sunlight etc. can be the cause of activation of the virus. From a practical viewpoint the herpes viruses typically cause a skin rash as a major manifestation.

Two main types of herpes simplex viruses are known, HSV-1 causing oral herpes and HSV-2 causing genital herpes. The viruses cause reoccurring, painful skin and mucosa lesions in about 10% of the population. The pain and cosmetic effects of the disease are of primary concern for most patients and pain relief and more rapid healing would represent a major advance in the art. It is essential to note that healing occurs spontaneously in most patients and one major object of the effort should therefore be directed to hasten the healing process and to provide analgesic effect.

SUMMARY OF THE INVENTION

The present invention has for its main object to provide for new techniques for the prevention or treatment of infection disease caused by herpes virus in mammals including man.

Another object of the invention is to provide for a new combination of active ingredients to be used for the manufacture of a medicament for such prevention or treatment.

Yet another object of the invention is to provide a process for the treatment of infections in mammals including man caused by herpes virus.

For these and other objects which will be clear from the following disclosure the invention provides for new techniques residing in the use of heparin or heparan sulphate in combination with chlitosan for the manufacture of a medicament for the prevention or treatment of infectious diseases caused by herpes virus in mammals including man.

In such use it is preferred that the manufacture of said medicament is based on a combination of heparin and chitosan.

Both heparin and heparan sulphate are commercially available on the market from several manufacturers. Also partially hydrolyzed forms of these ingredients can be used provided that their biological activity remains substantially unaltered.

The medicament to be used to prevent or combat infectious disease caused by herpes viruses can be presented in different physical forms, for example as powders, ointments, pastes, gels, suspensions or solutions. The form to be used is, of course, adapted to the nature of the disorder to be treated.

One of the main components in the present medicament is the polysaccharide chitosan which is a linear 1,4-bound polysaccharide built up from β-D-glucoseamine entities. The chitosan is manufactured by N-deacetylation of chitin, a polymer which forms the shell of inter alia insects and crayfish. Commercial chitin is recovered from crab and shrimp shells which constitute waste products from the fishing industry. By regulating the alkali treatment of chitins it is possible to manufacture chitosans of varying degrees of N-acetylation. When treating chitin with alkali, such as sodium hydroxide, N-deacetylation takes place wherein acetamido groups are converted to amino groups thus forming chitosan.

The physical properties of chitosan affecting its utility depend on the degree of N-acetylation, molecular weight and homogeneity. Chitosan is biodegradable, both by chitinas from the digestive system and by lysozyme in body fluids.

It is preferred in connection with the use of the present invention that the chitosan has a degree of N-acetylation of at most about 90% and preferably at most about 50%. It is particularly preferred that the degree of N-acetylation is less than about 25%.

The two main components of the medicament involved in the present invention, heparin or heparan sulphate and chitosan, are suitably used in combination with conventional carriers or excipients of a medicinally acceptable character. Quite generally it is preferred that the matrix is an aqueous matrix, and the carrier or the excipient may contain a viscosity-increasing polysaccharide, which can be selected from hemicelluloses, for example arabino xylanes and glucomannanes, plant gums, for example guar gum, locust bean gum, celluloses and derivatives thereof, for example methylcellulose, ethylcellulose, hydroxiethylcellulose, carboximethylcellulose, starch and starch derivatives, for example hydroxiethylstarch or crosslinked starch, microbial polysaccharides, for example xanthan gum, curdlan, pullulan, dextran. Also algi polysaccharides, for example agar, carrageenans, alginic acid, can be used as a constituent in the carrier or excipient.

A preferred polysaccharide for use in the carrier or excipient is a cellulose derivative, for example methylcellulose.

In the subject medicament it is preferred that the combined amount of viscosity-increasing polysaccharide and said chitosan is less than about 10% by weight based on the total weight of the medicament.

A preferred physical form of the medicament is the gel form, and in such gel-formed medicament said combined amount of polysaccharide and chitosan is preferably within the range about 0,5 to about 5% by weight based on the medicament as a whole.

Said heparin or heparan sulphate is preferably present in the medicament in an amount of from about 0,1 to about 2% by weight.

The present invention also provides for a process for the prevention or treatment of infectious diseases in mammals including man caused by herpes viruses. This process comprises the step of applying onto a site in need of treatment an active amount of a medicament containing in combination heparin or heparan sulphate and chitosan.

EXAMPLES OF EMBODIMENTS

The present invention will in the following disclosure be illustrated in connection with non-limiting examples. In said examples parts and percentages refer to weight if not otherwise stated. This illustration is made in association with the appended drawing, wherein:

BRIEF DESCRIPTION OF THE FIGURE

The effect of HSV-1 plaques is plotted against serial sample dilution for compositions of example 1–5 illustrating complete medicament and compositions excluding one or more constituents.

Example 1
Preparation of complete medicament

The hydrochloride salt of chitosan having an N-deacetylation degree of 16% (Pronova Biopolymers, Drammen, Norway) is dissolved in sterile filtered distilled water to form a 3% solution of the chitosan.

A 0,6% solution of native heparin containing methylcellulose in a concentration of 4 g/L is prepared.

Both solutions are autoclaved and admixed under sterile conditions in equal parts. Sorbic acid is added as a preservative in an anti-fungal amount.

Example 2

The composition of Example 1 is prepared in a similar manner but excluding the sorbic acid.

Example 3

The composition of Example 1 is prepared in a similar manner but excluding sorbic acid and heparin.

Example 4

The composition of Example 1 is prepared in a similar manner but this time excluding sorbic acid and chitosan.

Example 5

The composition of Example 1 is prepared in a similar manner but this time excluding, in addition to sorbic acid and heparin, also chitosan.

Example 6
Experimental procedure

The diluent used in the experiments is isotonic NaCl (0.136 M) and Eagle Minimum Essential Medium (EMEM). The virus used is HSV-1, strain KOS321.

The samples are diluted in 24 well plates. 1 mL of sample is mixed with 1 mL of isotonic NaCl and then serial 2-fold dilutions in isotonic NaCl up to a dilution of 1:32 are performed. The last well in each row contains only isotonic NaCl. The same solutions are also made in EMEM instead of isotonic NaCl.

Detailed procedure:
1. Add 100 PFU of HSV-1 in 100 $\mu$L of isotonic NaCl to serial dilutions of sample.
2. Incubate for 10 min at RT.
3. Wash the cells (Green monkey kidney cells (GMK AH1), confluent monolayers, 3 days old, 6 well plates) 1× with 2 mL of either isotonic NaCl or EMEM.
4. Add 1 mL of virus-sample mixture to cells.
5. Incubate for 1 h at RT.
6. Wash the cells 2× with 2 mL of EMEM.
7. Add 3 mL of standard methylcellulose solution.
8. Incubate for 3 days in $CO_2$ incubator at 37° C.
9. Stain the cells with crystal violet solution and count the viral plaques.

Results

The appended drawing shows by way of diagram the results as HSV-1 plaques plotted against the sample dilution (neg. log2). It can be seen from the results illustrated in the drawing that a dilution of 1:2 and 1:4 resulted in inhibition by all preparations probably due to the presence of methylcellulose. In dilutions 1:16 and 1:32 only the preparations containing heparin are active. Up to a dilution of 1:32 the inhibitory effect of the preparations containing both heparin and chitosan was maintained.

Test for toxicity have shown that all compositions were non-toxic vis-à-vis GMK cells.

Example 7
Clinical tests

The following clinical testing was made using a composition in accordance with Example 1 above in the form of a gel. All tests were directed to the prevention or treatment of orolabial infection caused by HSV-1 virus.

Case 1

A 15 year old boy was repeatedly treated, both by prophylactic treatment of early symptoms and treatment of established infection. Local application of the composition of Example 1 eliminated early symptoms within 24 hours and provided healing in 72 hours, respectively.

Case 2

A 48 year old male was treated prophylactically for early symptoms, the result being the same as in Case 1 above.

Case 3

A 9 year old female has successfully used the medicament of Example 1, both against established disease and in prophylactic treatment.

Case 4

A 3 year old boy having fully developed lip infection was topically treated with the composition of Example 1 above. This resulted in arrested infection in 2 days and healing in 4 days.

Case 5

A 52 year old male has successfully used the gel of Example 1 both for the treatment of established disease and for prophylactic treatment of early symptoms.

The results presented above relating both to inhibition of virus cell growth and clinical testing all verify the astonishing effect the present compositions have on the infectious disease caused by herpes viruses. The fact that such infections could be successfully treated using a combination of heparin and chitosan was in fact unexpected and surprising. Although the invention is not restricted to any particular theory or mechanism of action it may be that the matrix used in the composition provides for slow release of the heparin in an active form. The matrix including chitosan can be considered to bind the heparin by ionic bonds so that it will not be inactivated by enzymes present in the environment of treatment, such as the enzyme heparinas. This was clearly unexpected in view of the sensitivity of heparin to enzymatic degradation and inactivation.

It is to be noted that the invention as exemplified above is not restricted to the presented embodiments since modifications are obvious to the skilled artisan. Therefore, the scope of the invention is only restricted by the appended claims.

What is claimed is:

1. A method for treating or preventing herpes infection in a subject in need of such treatment or prevention by administering a medicament comprising a prophylactically or therapeutically effective amount of heparin and chitosan or heparan sulfate and chitosan.

2. The method of claim 1, wherein said medicament comprises heparin and chitosan.

3. The method of claim 1, wherein said chitosan has a degree of N-acetylation of at most 90%.

4. The method of claim 3, wherein said degree of N-acetylation is at most 50%.

5. The method of claim 1, wherein said medicament comprises a pharmaceutically acceptable carrier or excipient.

6. The method of claim 1, wherein the medicament is in a form selected from the group consisting of a powder, an ointment, a paste, a gel, a suspension, a solution, and a film.

7. The method of claim 5, wherein said carrier or excipient comprises a viscosity-increasing polysaccharide.

8. The method of claim 7, wherein said viscosity-increasing polysaccharide is a cellulose derivative.

9. The method of claim 1, wherein said medicament comprises an aqueous matrix.

10. The method of claim 7, wherein said viscosity-increasing polysaccharide and said chitosan in combination constitute less than 10% by weight of said medicament.

11. The method of claim 6, wherein said medicament is in the form of a gel.

12. The method according to claim 5, wherein said viscosity-increasing polysaccharide and said chitosan together constitute from about 0.5 to 5.0% by weight of said medicament.

13. The method according to claim 11, wherein the amount of said heparin or heparan sulfate in said medicament ranges from about 0.1 to 2.0% by weight.

* * * * *